United States Patent [19]
Senda et al.

[11] Patent Number: 5,397,451
[45] Date of Patent: Mar. 14, 1995

[54] CURRENT-DETECTING TYPE DRY-OPERATIVE ION-SELECTIVE ELECTRODE

[75] Inventors: Mitsugi Senda; Katsumi Hamamoto; Hisashi Okuda, all of Kyoto, Japan

[73] Assignee: Kyoto Daiichi Kagaku Co., Ltd., Kyoto, Japan

[21] Appl. No.: 187,067

[22] Filed: Jan. 27, 1994

[30] Foreign Application Priority Data

Jan. 29, 1993 [JP] Japan .................... 5-013883

[51] Int. Cl.[6] .......................................... G01N 27/26
[52] U.S. Cl. .................... 204/418; 204/403; 422/82.03; 435/817; 435/288; 435/291
[58] Field of Search ............... 204/418, 403, 435; 422/82.03; 435/817, 288, 291

[56] References Cited

U.S. PATENT DOCUMENTS

| 3,856,649 | 12/1974 | Genshaw et al. | 204/418 |
| 4,040,929 | 8/1977 | Bauer et al. | 204/195.5 |
| 4,929,313 | 5/1990 | Wrighton | 204/418 |
| 5,271,820 | 12/1993 | Kinlen et al. | 204/418 |
| 5,312,590 | 5/1994 | Gunasinghana | 204/403 |

FOREIGN PATENT DOCUMENTS 0309067  3/1989  European Pat. Off. .

OTHER PUBLICATIONS

Osakai et al., Analytical Sciences, 3, 521–526 (1987) *no month available.

Primary Examiner—John Niebling
Assistant Examiner—Bruce F. Bell
Attorney, Agent, or Firm—Birch, Stewart, Kolasch & Birch

[57] ABSTRACT

A current-detecting type dry-operative ion-selective electrode having a working electrode and a counter electrode which are mounted on an insulating substrate, a first electrolyte layer containing a hydrophilic polymer and an ion-sensitive layer containing a hydrophobic polymer which are formed on the working electrode, and a second electrolyte layer containing a hydrophilic polymer which is laminated over the whole electrode system.

5 Claims, 4 Drawing Sheets

CURRENT-DETECTING TYPE DRY-OPERATIVE ION-SELECTIVE ELECTRODE

BACKGROUND OF THE INVENTION:

1. Field of the Invention

The present invention relates to a current-detecting type dry-operative ion-selective electrode. More particularly, the present invention relates to make an electrochemical sensor dry-operative, which is used to measure quickly and simply the presence and an amount of a specific material in a sample to be assayed utilizing a polarization in a voltammeteric electrochemical analysis.

2. Description of the Related Art

In these years, a measurement using an electrochemical sensor has been widely used in the medical field.

For example, a potential-detecting type ion-selective electrode (hereinafter referred to as "ISE") is widely used as a safe and handy analytical element which requires no gas cylinder, in place of analysis of sodium or potassium ion by a conventional flame photometric detection or analysis of chloride ion by a coulometric titration. Recently, a disposable dry-operative plate form ISE is proposed to measure a concentration i of an electrolyte in a body fluid, and a portable exclusive system which performs the measurement more quickly and easily is commercialized.

Japanese Patent KOKAI Publication Nos. 287146/1990 and 287155/1990 disclose such disposable plate form ISE and the exclusive measuring equipment therefor.

In such ISE, a functional film is formed by covering a surface of a silver/silver chloride electrode with an electrolyte layer and a sensitive material which is reactive with a specific ion, and the functional film is contacted to the sample to be assayed to detect the presence of the specific ion in the sample from a potential response which is proportional to a logarithm of the ionic activity.

A current-detecting type ISE is a novel ion-selective electrode which can detect an ion (or electron) moving reaction at an interface between two immiscible electrolyte solutions, namely an oil-water interface by a method similar to conventional polarography or voltammetry. With this ISE, since the response of current is proportional directly to the ion concentration, very accurate measured values can be obtained in a limited concentration range of the specific material as in the body fluid. If an interfering ion is present, a curve due to the interfering ion appears on a voltamogram (a current-potential curve) in addition to the curve due to the target ion. When half-wave potentials of the both ions are separated by a suitable distance, the influence of the interfering ion can be corrected.

From another point of view, two or more kinds of ions can be quantitatively measured at the same time. Such is reported by J. Koryta, Electrochim. Acta, 33, 189 (1988) and M. Senda, et al, Electrochim. Acta, 36, 253 (1991).

However, since the potential response measured by the conventional potential-detecting type ISE is proportional to the logarithm of the ion activity, the potential-detecting type ISE is suitable for measuring the material in a wide range of concentration. However, an error in the measured value in the very narrow concentration range as in the body fluid cannot be neglected clinically.

Theoretically, $\pm 1$ mV error in the potential value will produce $\pm 4\%$ error in the case of the Nernst response of a monovalent ion. In fact, the error of about $\pm 1$ mV is unavoidable due to the influence of co-present material in the analysis, and such error will make a trouble when the accurate ion concentration should be known.

In contrast, the current-detecting type ISE is excellent in accuracy. However, many problems should be solved before its practical use. For example, a method for producing a probe type (cylindrical) current-detecting type ISE shown in FIG. 1 is proposed by T. Osakai et al, Anal. Sci., 3,521 (1987). This probe type ISE comprises a dialysis membrane 2 which is fixed to a glass tube 1 by a polytetrafluoroethylene tube 3. At a bottom of the glass tube, an ion-sensitive liquid 4 comprising dissolved nitrobenzene using a micro-syringe gently. Over the ion-sensitive liquid 4, an internal liquid 5 is poured, and a silver/silver chloride electrode 6 is dipped in the liquid 5 to assemble the film coated ISE. At an end of a slightly thick glass tube 7 in which the film coated ISE can be inserted, a polytetrafluoroethylene film 8 and a nylon mesh 10 as a spacer to hold the inner liquid are laminated. Over the end portion of the glass tube 7, a tetrafluoroethylene tube 11 is covered. Then, the film coated ISE is inserted in the glass tube 7 till it reaches the bottom of the glass tube 7. Between the glass tube 1 and the glass tube 7, an internal liquid 9 is poured. In the internal liquid 9, a silver/silver chloride electrode 6 wound around a glass tube is dipped. All the elements are fixed to prevent displacement of the elements. As understood, this electrode has a very complicated structure, and very high skill is required to assemble the polytetrafluoroethylene film, to pour the ion-sensitive liquid and the internal liquids. In addition, stability in time is not good. Therefore, since it is impossible to assemble a number of ISEs and store them, each ISE should be assembled when it is used. Thus, this ISE is not practically attractive.

Japanese Patent KOKAI Nos. 168045/1985, 88134/1986 and 175656/1987 disclose a method for solidifying the ion sensitive liquid, or a method for producing a minute film coated ISE. However, these methods cannot solve the troublesome assembling steps of the electrode or the necessity of skill. The handling property or the long-term stability of the produced ISE is not satisfactory. Further, there are still many problems to be solved relating to the product difference such as deviation of the resistance of the sensitive film or the response speed, the influence of the electrode surface or the electrode shape on the current, and the like.

SUMMARY OF THE PRESENT INVENTION

An object of the present invention is to provide a disposable plate form dry-operative electrode, which is simple and cheap and makes extensive use of the characteristics and the properties of the current-detecting type ISE.

To achieve this and other objects, the current-detecting type ISE of the present invention comprises a plate form ISE which can be mass produced by screen printing, which can produces the ISE having stable quality.

According to the present invention, there is provided a current-detecting type dry-operative ion-selective electrode comprising a working electrode and a counter electrode which are mounted on an insulating substrate, a first electrolyte layer containing a hydrophilic polymer and an ion-sensitive layer containing a hydrophobic polymer which are formed on said working electrode, and a second electrolyte layer containing a hydrophilic polymer which is laminated over the whole electrode system.

DETAILED DESCRIPTION OF THE INVENTION

Figure 1:
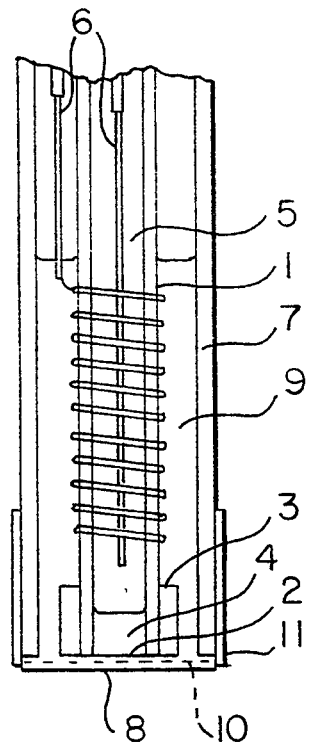
FIG. 1 is a cross sectional view of a conventional probe type current-detecting type ISE.

According to the present invention, the functional film of the electrochemical sensor is formed as follows:

The electrode system comprising the working electrode and the counter electrode are formed on the insulating substrate from a conductive material such as a silver paste or a carbon paste by screen printing, and circles of resist ink are formed around the peripheries of the working electrode and the counter electrode. In an dent area around the working electrode encircled by the resist ink, a first electrolyte solution in the form of a solution of a hydrophilic polymer is coated and dried to form the first electrolyte layer, and then an ion-sensitive material solution in the form of a solution of a hydrophobic polymer is coated and dried to form the ion-sensitive layer. Thereafter, over the working and counter electrodes, a second electrolyte solution in the form of a solution of a hydrophilic polymer is coated and further a solution of a hydrophilic or hydrophobic polymer is coated and dried to form the functional film.

By the method for forming the functional film of the electrochemical sensor according to the present invention, since the working and counter electrodes are formed by the screen printing, a surface area of each electrode is made uniform. In addition, each electrolyte layer and the ion-sensitive layer are formed by coating the solutions in the dent areas encircled by the resist ink, a thickness of each layer can be made uniform, and a very thin functional film can be formed. Thereby, a solution resistance can be made small, and a stable output is obtained. Further, according to the present invention, the production of the ISE is easy and the production cost is low. Accordingly, the disposable. current-detecting type ISE including the electrode system can be provided.

As the materials forming the functional thin film to be used in the formation of the sensitive layer of the electrochemical sensor according to the present invention, the following materials are suitable:

As a gel material forming a matrix of the first and second electrolyte layers, polyvinylpyrrolidone, polysodium acrylate, carboxymethylcellulose, polyvinyl alcohol, gelatin, and the like are exemplified. They may be used as a mixture of two or more of them.

As a humectant, at least one of polyethylene glycol, glycerol, pyrrolidonecarboxylic acid, sorbitol and nonionic surfactants is used.

As a matrix material of the ion-sensitive layer, polyvinyl chloride, vinyl chloride-vinyl acetate copolymer, polycarbonate, polyurethane, epoxy resin, silicone resin, polyester acrylic resin, polyvinyl butyral resin, and the like are exemplified.

As the sensitive material, there can be used an ionophore such as benzo-18-crown-6, dibenzoi30-crown-10, biscrown ethers nonactin, monactin, valinomycin, citianine B, quaternary ammonium salts, and the like according to a material to be measured.

As a plasticizer, nitrobenzene, dichloroethane, o-nitrophenyl octyl ether, o-nitrophenyl phenyl ether, 2-fluoro-2'-nitrophenyl ether, dioctyl phthalate, dioctyl adipate, dioctyl sebacate, and the like are added.

When the hydrophilic layer is required to cover the second electrolyte layer, carboxymethylcellulose, polysodium acrylate, agar, polyvinyl alcohol, gelatin, polyvinylpyrrolidone, and the like is used, while when the hydrophobic layer is required, Nafion (a trade name of DuPont), polyvinyl chloride, polyurethane epoxy resin silicone resin and the like are used When the electrode of the present invention is an ammonium ion-selective electrode, the surface of the second electrolyte layer is covered with the polymer layer and, over the polymer layer, a solid layer from a mixture of a protein, glutaraldehyde and an enzyme, is formed. When the enzyme is urease or creatininedeiminase, then urea or creatinine is measured, respectively. In addition, an enzyme activity of leucineaminopeptidase, Σiglutamyltransesterase or the like which generates an ammonium ion through a certain reaction may be measured.

The present invention is not limited by the above examples. Various applications and modifications can be contemplated. For instance, in the above examples, the working and counter electrodes are arranged at concentric positions as the basic structure of FIG. 2, while they may be arranged in any form insofar as a liquid bridge is formed between them. As the conductive material of the working and counter electrodes, any conductive material such as platinum, carbon, graphite, etc. may be used in addition to the silver/silver chloride electrode.

In addition to the above exemplified materials, a suitable ionophore or a complex-forming compound may be used to provide the electrode with the selectivity to the specific ion or an organic material, whereby a spectrum of the materials to be measured can be widened.

PREFERRED EMBODIMENTS OF THE INVENTION

The present invention will be explained by the following Examples and Comparative Examples with making reference to the accompanying drawings.

Figure 2:
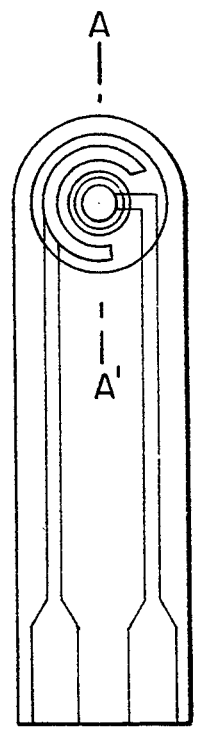
FIG. 2 is a plan view of one example of the plate form ISE according to the present invention, in which a current-detecting type ISE is mounted on the insulating substrate.
Figure 3:
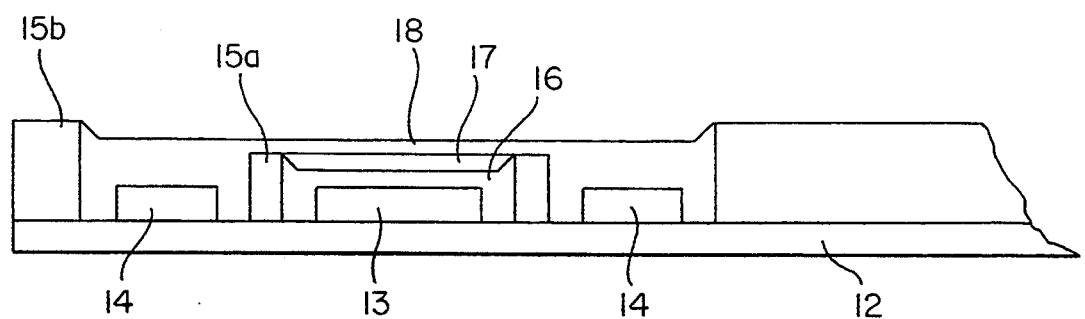
FIG. 3 is an enlarged cross sectional view of the plate form ISE of FIG. 2 along the line A—A'.

FIG. 2 is a plan view of an example of the plate form electrode comprising a current-detecting type ISE formed on an insulating electrode, and FIG. 3 is an enlarged cross sectional view of the electrode of FIG. 2 along the line A—A'.

On a substrate 12 made of, for example, polyethylene terephthalate, an electrode system consisting of a working electrode 13 and a counter electrode 14 was formed by printing a silver paste was by screen printing and heat drying them. Insulating parts 15a and 15b were formed by screen printing a liquid form polymer resist comprising a polyvinyl chloride as a main solid component around each of the working electrode and the counter electrode and heat drying it so that the working electrode 13 and the counter electrode 14 were present at the bottoms of the respective formed dent portions.

A surface of each of the formed silver layers was treated with an aqueous solution containing 16 mM hydrochloric acid and 36 mM potassium dichromate (oxidation-halogenation treatment) for about 60 seconds, washed with water and dried to form silver chloride on the surface of the silver layer, whereby the working electrode 13 and the counter electrode 14 were changed to the silver/silver chloride electrodes.

In the dent portion around the working electrode 13 surrounded by the insulating part 15a, a first electrolyte solution 16 was coated and dried at 50° C. for 10 minutes. This first electrolyte solution was prepared by dissolving 20 mM tetrapentylammonium chloride (hereinafter referred to as "TPenACl") and 10 mM magnesium chloride in an aqueous solution containing 0.25% of carboxymethylcellulose (hereinafter referred to as "CMC") as a hydrophilic polymer and 0.2% of glycerol as a humectant. On the first electrolyte layer 16, a potassium ion-sensitive material composition containing the following components Was coated and dried at 50° C. for 10 minutes to form an ion-sensitive layer 17:

| Potassium ion-sensitive material composition: | |
|---|---|
| Tetrahydrofuran | 10 ml |
| Polyvinyl chloride (polymerization degree: 1100) | 1 g |
| Nitrophenyl octyl ether | 2 g |
| Tetrabutylammonium tetraquis(4-chlorophenyl)-borate | 29 mg |
| Valinomycin | 8 mg |

Then over the whole electrode system, namely over the potassium ion-sensitive layer 17, the counter electrode 14 and the insulating part 15b, an aqueous solution containing 0.5% of CMC, 0.2% of glycerol and 10 mM of magnesium chloride was coated and dried at 50° C. for 15 minutes to form a second electrolyte layer 18.

The thickness of each layer was determined by an amount of the contained polymer and an amount of the coated solution (usually from 3 to 10 μl). Preferably, the thickness of each of the first electrolyte layer 16 and the ion-sensitive layer 17 is from 5 to 200 μm, and that of the second electrolyte layer 18 is from 5 to 500 μm.

In the above example, the current-detecting type ISE for measuring the potassium ion is explained. To assemble the ISE for measuring other ion, a sensitive material for the other ion is used. For example, to form a sensitive layer selective to the sodium ion, bis-12-crown-4 is used as a sensitive material, and to form a sensitive layer selective to the chloride ion, a quaternary amine is used in place of valinomycin used in the above example.

Figure 4:
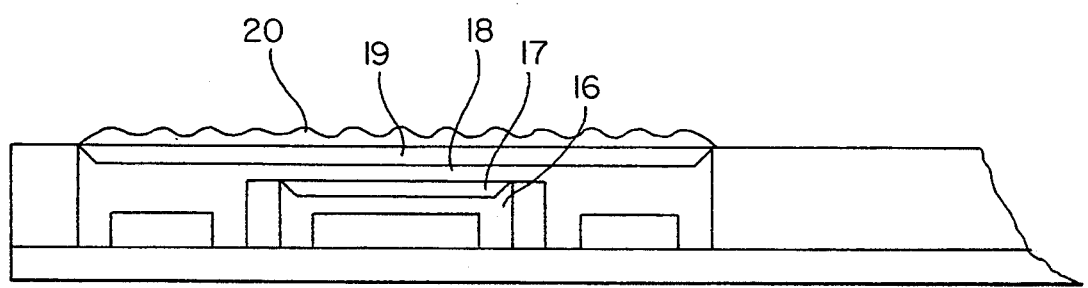
FIG. 4 is a modification of the ISE of FIG. 3 using an enzyme electrode.

FIG. 4 shows a cross sectional view of another example of the current-detecting type dry-operative ion-selective electrode according to the present invention. The basic structure of this electrode is substantially the same as that of the electrode of FIG. 3 except that the ion selective layer 17 is formed to selectively respond to the ammonium ion, and an immobilized enzyme layer 20 is formed on the hydrophobic polymer layer 19.

The first electrolyte layer 16 was formed from an aqueous solution containing 0.25% of CIVIC and 0.2% of glycerol in which 100 mM tetrabutylammonium chloride was dissolved, and the ion-selective layer 17 contained dibenzo-18-crown-6 in place of valinomycin of the previous example.

The second electrolyte layer 18 was formed from an aqueous solution containing 0.25% of CMC and 0.2% of glycerol in which 50 mM magnesium chloride and 50 mM L-lysine and having pH of 8.5 in the same manner as above. Then, an alcoholic solution of Nafion (a trade name of DuPont) was coated directly on the second electrolyte layer 18 and dried at 40° C. for 5 minutes to form a hydrophobic polymer layer 19.

On the center area of the polymer layer 19, a solution of urease (100 units) in 100 mM tris-hydrochloric acid buffer (pH 8.5) containing 15% of bovine serum albumin and 3% of glutaraldehyde was coated and kept standing at 25° C. for 3 hours followed by drying at 40° C. for 15 minutes to form a urea sensor.

In the above case, both the hydrophobic polymer layer 19 and the immobilized enzyme layer 20 were formed by the coating method. The thickness of each layer is determined by the solid content and the coating amount of the solution (usually from 5 to 20 μl). After drying, each thickness is preferably from 5 to 300 μm.

Figure 5:
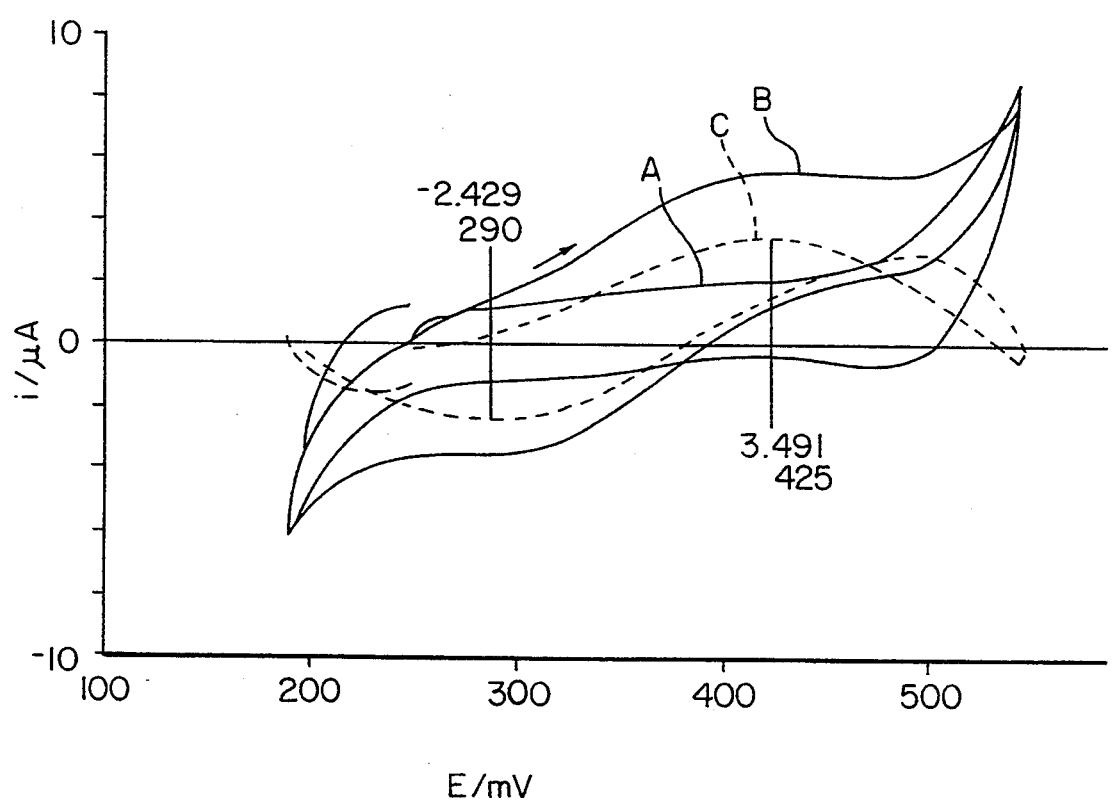
FIG. 5 shows cyclic voltamograms, when potassium ion in an aqueous solution is measured with the current-detecting type ISE of FIG. 3.

FIG. 5 shows a cyclic voltamogram when the potassium ion in an aqueous solution was analyzed using the current-detecting type ISE of FIG. 3.

As an indicating electrolyte, 10 mM magnesium chloride was used, and as the potassium ion, 5 mM potassium chloride was used.

The potential sweeping was carried out between 190 mV and 550 mV, and the current was measured by a pulse application method.

In FIG. 5, the curve A is a cyclic voltamogram when the sample contained only the indicating ion, while the curve B is a cyclic voltamogram when the sample contained the potassium ion. The curve C is the cyclic voltamogram of the potassium ion alone, which is obtained by deducting the value of the curve A from that of the curve B.

Figure 6:
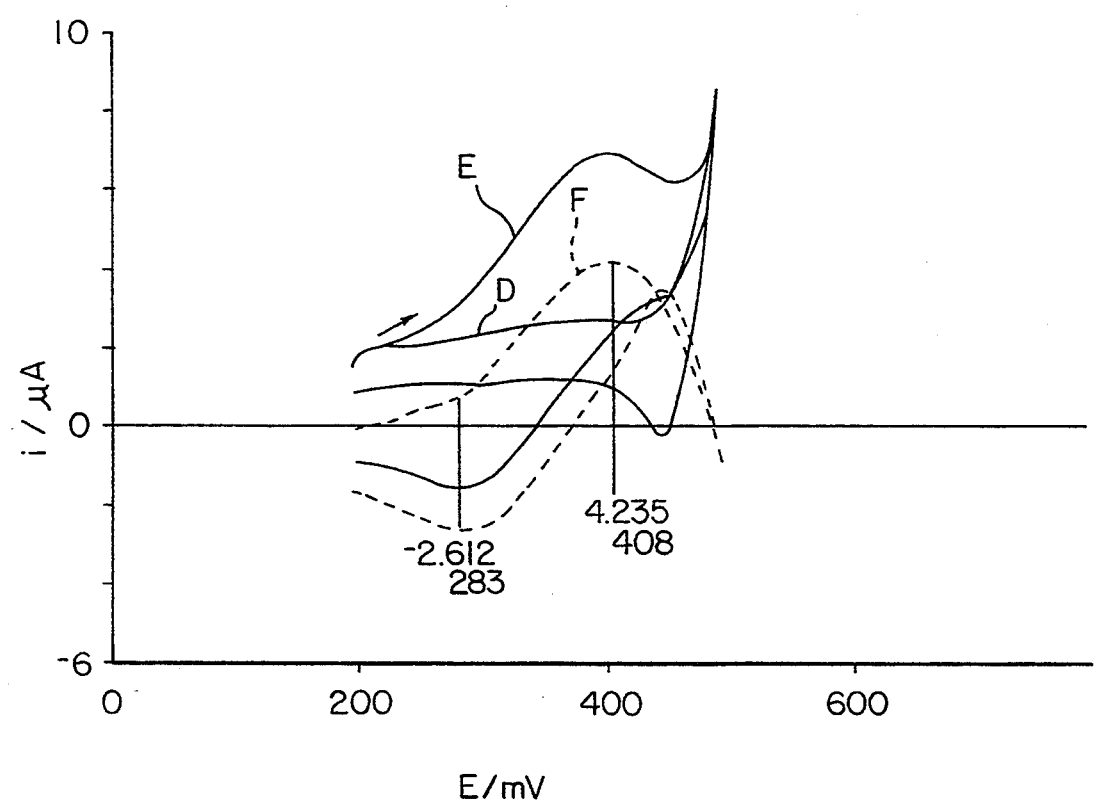
FIG. 6 shows cyclic voltamograms, when urea is measured using the enzyme electrode of FIG. 4.

FIG. 6 is a voltamogram when a commercially available control serum (Monitol 1.ll, manufactured by DADE) was measured with the urea sensor using the current-detecting type ammonium ISE as a ground electrode.

In FIG. 6, the curve D is a cyclic voltamogram of 100 mM tris-hydrochloric acid buffer (pH 8.5) containing no urea, while the curve E is a cyclic voltamogram when 40 mg/dl of urea was contained. Then, the curve F is the cyclic voltamogram of the net urea, which is obtained by deducting the value of the curve D from that of the curve E.

In the practical assay, a potential pulse having the same intensity is applied to the potential at which the critical current value is obtained, and a responses current value is recorded.

In the above experiments, the base currents expressed by the curves A and D were measured. According to the present invention, the measurement of the base current may not be necessary, since the performance and quality of the ISE are stable.

EFFECTS OF THE INVENTION

According to the current-detecting type ISE of the present invention, since the working electrode and the counter electrode are formed by screen printing, their electrode surface areas are constant. In addition, the electrolyte layers and the sensitive layer are coated by screen printing in the areas surrounded by the resist ink, a coated area is constant and all the layers have the uniform thicknesses. Furthermore, the very thin functional film can be formed. Thereby, the ISE will generate a small output because of the low membrane resistance, and the measuring performance can be greatly increased. The present invention provides a cheap disposable current-detecting type ISE which is easily produced and has stable quality.

What is claimed is:

1. A current-detecting type dry-operative ion-selective electrode comprising a working electrode and a counter electrode which are mounted on an insulating substrate, a first electrolyte layer containing a hydrophilic polymer and an ion-sensitive layer containing a hydrophobic polymer which are formed on said working electrode, and a second electrolyte layer containing a hydrophilic polymer which is laminated over the whole electrode system.

2. The current-detecting type dry-operative ion-selective electrode according to claim 1, wherein each of said first and second electrolyte layers comprises a composition of at least one hydrophilic polymer selected from the group consisting of polyvinylpyrrolidone, polysodium acrylate, carboxymethylcellulose, polyvinyl alcohol and gelatin and at least one humectant selected from the group consisting of polyethylene glycol, glycerol, pyrrolidonecarboxylic acid, sorbitol and nonionic surfactants, and an electrolyte ion contained in said composition.

3. The current-detecting type dry-operative ion-selective electrode according to claim 1, wherein said ion-sensitive layer comprises a mass of polyvinyl chloride containing a plasticizer, an ion-sensitive material and a hydrophobic electrolyte.

4. The current-detecting type dry-operative ion-selective electrode according to claim 1, wherein said second electrolyte layer is covered with a hydrophilic or hydrophobic polymer layer.

5. The current-detecting type dry-operative ion-selective electrode according to claim 4, which is an ammonium ion-selective electrode, and which further comprises a solid-form mixture of a protein, glutaraldehyde and an enzyme on said hydrophobic or hydrophilic polymer layer.

* * * * *